United States Patent
Brinkman et al.

(10) Patent No.: US 8,357,661 B2
(45) Date of Patent: Jan. 22, 2013

(54) RECOMBINANT HUMAN ALPHA1-ANTITRYPSIN

(75) Inventors: Elisabeth C. M. Brinkman, Noordwijkerbout (NL); Cornelis E. Hack, Diemen (NL); Ingrid Van Den Nieuwenhof, Amsterdam (NL)

(73) Assignee: Crucell Holland B.V., Leiden (NL)

( * ) Notice: Subject to any disclaimer, the term of this patent is extended or adjusted under 35 U.S.C. 154(b) by 0 days.

(21) Appl. No.: 13/138,912

(22) PCT Filed: Apr. 20, 2010
(Under 37 CFR 1.47)

(86) PCT No.: PCT/EP2010/055177
§ 371 (c)(1),
(2), (4) Date: Apr. 26, 2012

(87) PCT Pub. No.: WO2010/127939
PCT Pub. Date: Nov. 11, 2010

(65) Prior Publication Data
US 2012/0214747 A1 Aug. 23, 2012

Related U.S. Application Data

(60) Provisional application No. 61/214,492, filed on Apr. 23, 2009.

(30) Foreign Application Priority Data

Apr. 23, 2009 (EP) ..................................... 09158640

(51) Int. Cl.
*A61K 38/14* (2006.01)

(52) U.S. Cl. ...... 514/20.9; 514/3.1; 514/20.1; 514/20.4; 530/350; 530/380

(58) Field of Classification Search ........................ None
See application file for complete search history.

(56) References Cited

U.S. PATENT DOCUMENTS

| 5,994,128 A | 11/1999 | Fallaux et al. |
| 2005/0164386 A1 | 7/2005 | Uytdehaag et al. |

FOREIGN PATENT DOCUMENTS

| WO | WO 00/63403 | 10/2000 |
| WO | WO 03/513927 | 6/2003 |
| WO | WO 2004/099396 | 11/2004 |
| WO | WO 2006/070011 | 7/2006 |
| WO | WO 2009/009086 | 1/2009 |
| WO | WO 2010/127939 | 11/2010 |

OTHER PUBLICATIONS

Chang, et al.; Improvement of glycosylation in insect cells with mammalian glycosyltransferases; Journal of Biotechnology 102 (2003) 61-71.
Garver, Jr. et al.; Production of glycosylated physiologically "normal" human$\alpha_1$-antitrypsin by mouse fibroblasts modified by insertion of a human$\alpha_1$-antitrypsin cDNA using a retroviral vector, Proc. Natl. Acad. Sci. vol. 84, pp. 10501054, Feb. 1987.
Kolarich, et al.; Biochemical, molecular characterization, and glycoproteomic analyses $\alpha_1$-proteinase inhibitor products used for replacement therapy; Transfusion vol. 46, Nov. 2006; pp. 19591977.
Kolarich, et al.; Comprehensive glycolproteomic analysis of human$\alpha_1$-antioypsin and its charge isoforms; Proteomics 2006, vol. 6; pp. 3369-3380.
PCT International Search Report PCT/EP2010/055177 dated Jul. 14, 2010.

*Primary Examiner* — Cecilia J Tsang
*Assistant Examiner* — Zachary J Miknis
(74) *Attorney, Agent, or Firm* — TraskBritt

(57) ABSTRACT

The present invention relates recombinant human α1-antitrypsin (rhAAT) comprising N-linked glycans, wherein at least 10% of said N-linked glycans are tetra-antennary glycans; and the degree of capping with sialic acid on said N-linked glycans (Z/A) is at least 50%. The invention further relates to rhAAT for use as a medicament, in particular for use in the prevention and/or treatment of a disease associated with AAT deficiency, and/or a disease involving neutrophil-mediated tissue damage.

17 Claims, 9 Drawing Sheets

FIG. 5
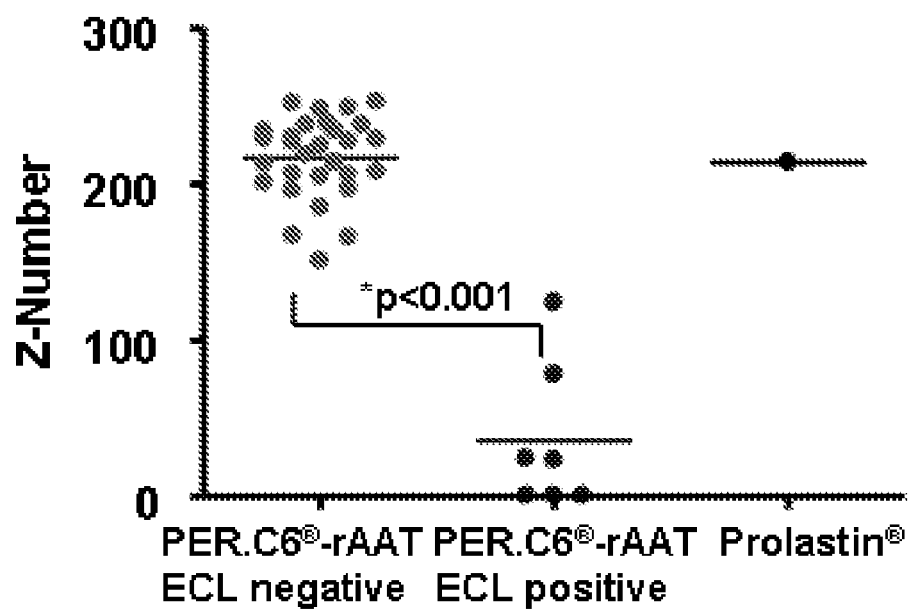
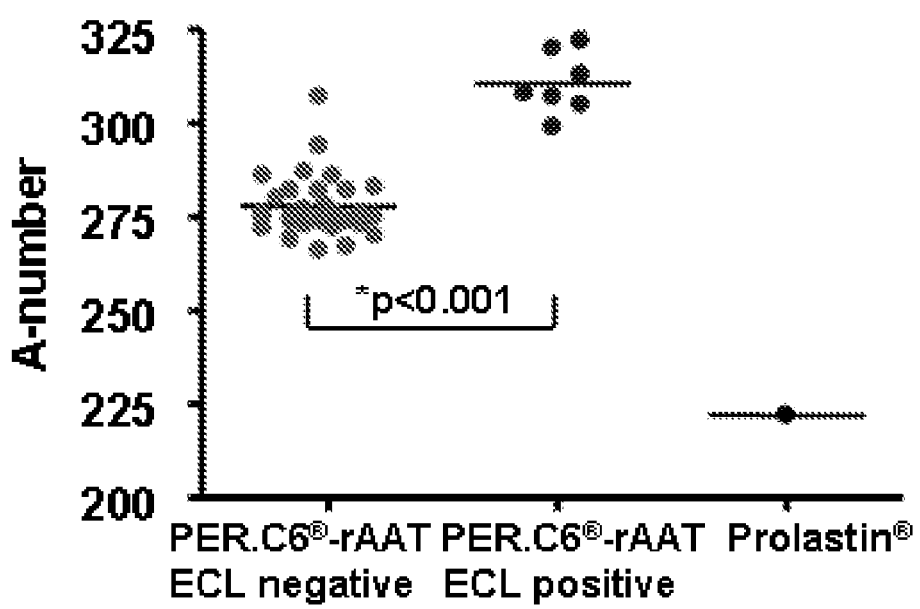

FIG. 9
A.
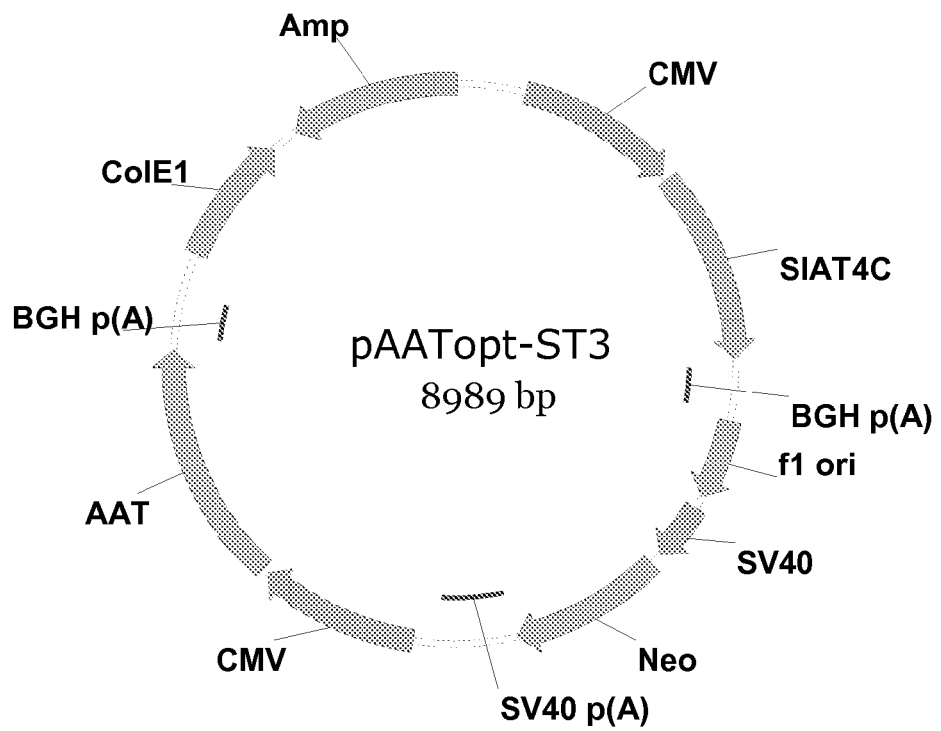
B.
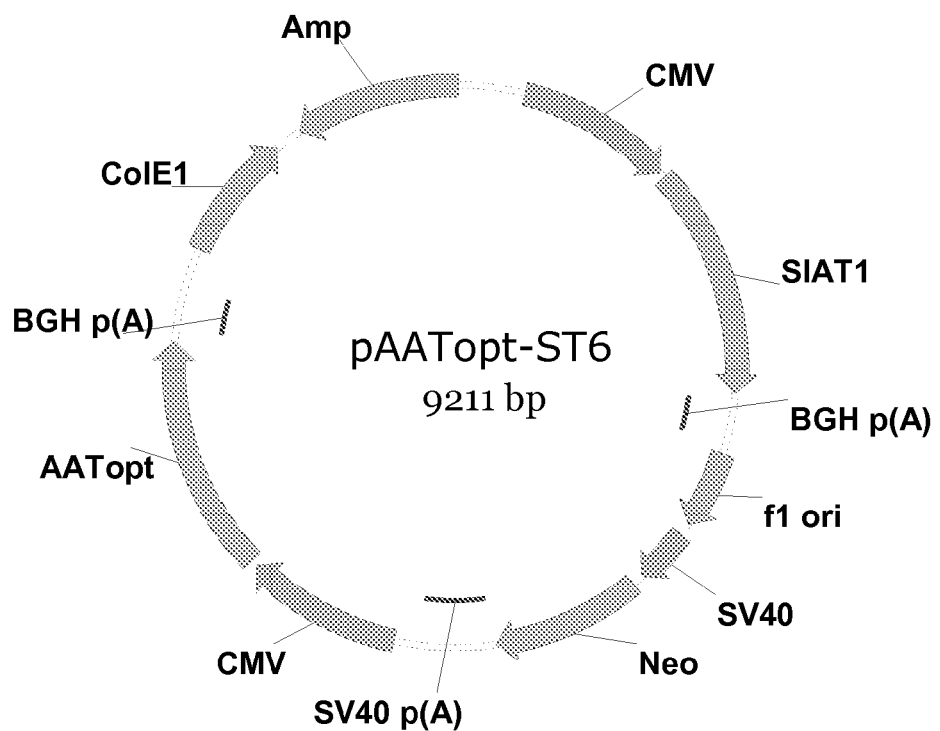

RECOMBINANT HUMAN ALPHA1-ANTITRYPSIN

CROSS-REFERENCE TO RELATED APPLICATIONS

This is a national phase entry under 35 U.S.C. §371 of International Patent Application PCT/EP2010/055177, filed Apr. 20, 2010, published in English as International Patent Publication WO 2010/127939 A1 on Nov. 11, 2010, which claims the benefit under Article 8 of the Patent Cooperation Treaty to European Patent Application Serial No. 09158640.4, filed Apr. 23, 2009, and benefit under 35 U.S.C. §119(e) U.S. Provisional Patent Application Ser. No. 61/214,492, filed Apr. 23, 2009.

TECHNICAL FIELD

The invention relates to the field of pharmaceutical products, in particular, to recombinant human α1-antitrypsin, that can be used for inter alia the prevention and/or treatment of α1-antitrypsin deficiency-related emphysema.

BACKGROUND OF THE INVENTION $\alpha_1$-Antitrypsin (AAT) or $\alpha_1$-protease inhibitor (α1PI) is a natural inhibitor of proteases released by activated neutrophils. AAT is a glycoprotein consisting of 394 amino acids and having a molecular weight of 52 kD. Human AAT is expressed as a 418-amino acid precursor from which a 24-amino acid precursor is clipped to yield the 394-amino acid final product. AAT is synthesized primarily in the liver, but expression has also been demonstrated in neutrophils, monocytes and macrophages.

Low or zero plasma levels of AAT constitute a risk factor for the development of emphysema due to the unopposed and destructive action of neutrophil proteases in the lungs. For the prevention and/or treatment of AAT deficiency-related emphysema, AAT augmentation therapy has been developed (Mulgrew et al., 2007).

Currently, patients with AAT-deficiency-associated emphysema are treated with a high dose of plasma-derived (pd)AAT (60 mg/kg/week; PROLASTIN® from Talecris, ARALAST® from Baxter and ZEMAIRA® from ZLB). Large quantities and frequent injections of AAT are required to relieve AAT-deficiency-related emphysema. A major concern with the plasma-derived material is the safety of the preparations. As with all human-derived material, potential risk of pdAAT is contamination with prions or other adventitious agents. A second concern is the limited availability of the plasma material.

Human plasma-derived AAT contains three N-linked glycans at Asn residues 46, 83 and 247. These glycans consist of mostly di- and tri-antennary structures. A high degree of sialylation of the glycans on recombinant proteins is of importance for optimal pharmacokinetics (PK).

Until now, recombinant production of AAT has been hampered by low expression in most recombinant platforms (Karnaukhova et al., 2006). Recombinant AAT has been produced at high levels in transgenic systems, but clinical development thereof has been stopped because of suboptimal pharmacokinetics (PK) and safety issues due to non-human contaminants (Spencer et al., 2005).

BRIEF SUMMARY OF THE INVENTION

It is now shown that recombinant human $\alpha_1$-antitrypsin (rhAAT) having a suitable pharmacokinetic profile can be produced in large quantities in PER.C6® cells.

In the research that led to this disclosure, cell lines expressing human AAT and co-expressing an α-2,3-sialyltransferase (ST3) or an α-2,6-sialyltransferase (ST6) were generated under serum-free conditions. The cell lines were capable of expressing high levels of rhAAT. Thus, yields of up to 22-picogram rhAAT per cell per day (pcd) were reached. Importantly, the rhAAT of the invention was shown to be active as a neutrophil elastase inhibitor. Analysis of the glycan profiles showed a good overall degree of capping with sialic acid. Interestingly, an increase in tetra-antennary glycans was noted on the rhAAT of the invention, as compared to plasma-derived AAT (PROLASTIN®). Furthermore, rhAAT produced in cells co-expressing ST3 showed an increased mean residence time (MRT) in rats, as compared to plasma-derived AAT. RhAAT produced in cells co-expressing ST6 showed a decreased mean residence time as compared to plasma-derived AAT.

In one aspect, provided is recombinant human α1-antitrypsin (rhAAT) comprising N-linked glycans, wherein:
(a) at least 10% of the N-linked glycans are tetra-antennary glycans; and
(b) the degree of capping with sialic acid on the N-linked glycans (Z/A) is at least 50%.

In another embodiment, at least 20% of the N-linked glycans are tetra-antennary glycans.

In a further embodiment, the degree of capping with sialic acid on the N-linked glycans that are tetra-antennary is at least 30%.

In a further embodiment, at least 50% of the total sialylation on the N-linked glycans is α-2,3-sialylation. Preferably, at least 90% of the total sialylation on the N-linked glycans is α-2,3-sialylation.

Also provided are preparations and pharmaceutical compositions comprising rhAAT and, optionally, one or more pharmaceutically acceptable excipients.

Also disclosed is the use of rhAAT, preparations and/or pharmaceutical compositions comprising rhAAT, for the prevention and/or treatment of inter alfa AAT-associated emphysema and/or inflammatory diseases with neutrophil-mediated tissue damage.

Also provided is a method for producing recombinant human α1-antitrypsin, comprising the steps of providing a PER.C6® cell with a nucleic acid encoding human α1-antitrypsin in such a way that the PER.C6® cell harbors the nucleic acid in an expressible form; and culturing the PER.C6® cell under conditions conducive to the production of recombinant human AAT, wherein the PER.C6® cell is modified to co-express α-2,3 sialyltransferase or α-2,6-sialyltransferase.

BRIEF DESCRIPTION OF THE FIGURES

FIG. 5. Sialylation (Panel A) and antennarity (Panel B) of the glycans of PER.C6-rAAT from ECL-negative samples in comparison with the glycans of PER.C6-rAAT from ECL-positive FIG samples and PROLASTIN®.

FIG. 9. Plasmid maps of the AAT expression vectors pAATopt-ST3 (Panel A) and pAATopt-ST6 (Panel B). CMV=Cytomegalovirus promoter, BGHp(A)=Bovine Growth Hormone polyadenylation sequence, f1 ori=f1 origin of replication, SV40=Simian Virus 40 promotor, Neo=Neomycin resistance marker, SV40p(A)=Simian Virus 40 poly-adenylation sequence, AAT=alpha$_1$-antitrypsin, Co1E1=Co1E1 origin of replication, Amp=ampicillin resistance marker, SIAT4C=gene coding for ST3=human sialyltransferase IV (L23767) (Panel A), SIAT1=gene coding for ST6=human sialyltransferase 1 (NM_003032).

DETAILED DESCRIPTION OF THE INVENTION

Figure 1:
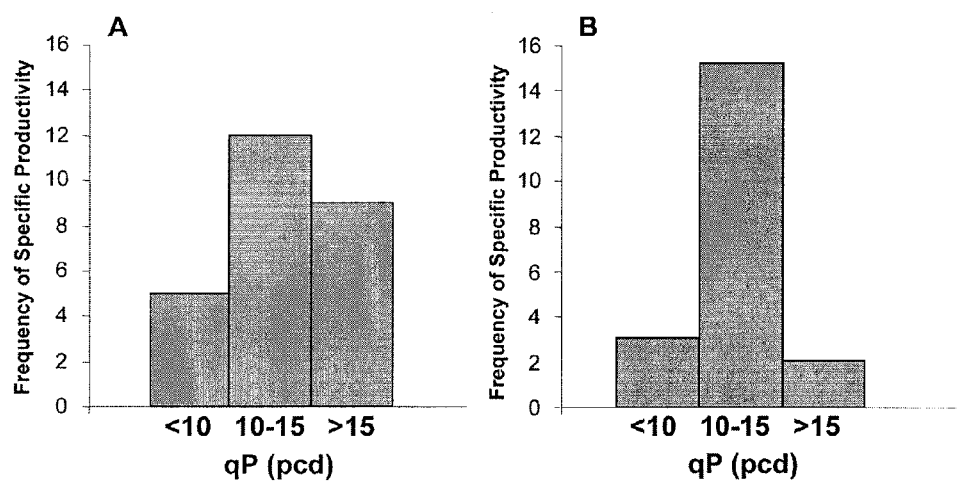
FIG. 1. Frequency distribution of the specific productivities of the batch cultures, both for cell lines overexpressing α-2,3 sialyltransferase (A: PER.C6-AAT-ST3) and cells overexpressing α-2,6-sialyltransferase (B: PER.C6-AAT-ST6).

Alpha$_1$-antitrypsin (AAT) is a natural inhibitor of proteases released by activated neutrophils. AAT is secreted into the blood plasma but its primary site of action is in the lung parenchyma. Human leukocyte elastase (FILE) (also known as human neutrophil elastase HNE), is a serine protease released from azurophilic granules of the neutrophils as part of the normal inflammatory response. Under normal homeostatic conditions AAT serves as an important regulator of proteolysis by human leukocyte elastase (HLE), thereby preventing damage of the lung alveolar matrix. Besides HLE, AAT also inhibits two other proteases released into the lungs by neutrophils, namely cathepsin G (catG) and protease 3 (Pr3).

Plasma-derived AAT products have been developed and are currently being used for the treatment of patients suffering from AAT-deficiency-related emphysema (i.e., having low or zero plasma AAT levels), such as PROLASTIN® (Talecris), ARALAST® (Baxter), and ZEMAIRA® (ZLB). High amounts (approximately 60 mg/kg/week) of this product are generally needed per patient. Besides emphysema, AAT is also a (potential) therapy for inflammatory diseases with neutrophil-mediated damage.

Recombinant production of AAT in, for example, *E. coli*, has been hampered by low expression in most recombinant platforms (Karnaukhova et al., 2006). Recombinant AAT has been produced at a high level in transgenic systems, but clinical development thereof has been stopped because of suboptimal pharmacokinetics (PK) and safety issues due to non-human contaminants (Spencer et al., 2005).

Provided herein is a recombinant human α1-antitrypsin (rhAAT) having suitable pharmacokinetic properties and that can be produced in large quantities in, for example, PER.C6® cells. The recombinant AAT hereof has been shown to be functionally active, as determined by a chromogenic assay based on inhibition of human neutrophil elastase, and to have promising pharmacokinetic properties, as compared to plasma-derived AAT products, such as PROLASTIN®.

Thus, provided is rhAAT comprising N-linked glycans, wherein
a) at least 10% of the N-linked glycans are tetra-antennary glycans; and
b) the degree of capping with sialic acid on the N-linked glycans (Z/A) is at least 50%.

N-linked glycans are sugar chains that are covalently linked to asparagine residues of a polypeptide (Varki et al., 1999). The process of N-glycosylation starts with the attachment of a dolichol oligosaccharide precursor to the asparagines precursor. This precursor is subsequently modified into a high-mannose, hybrid, or complex-type oligosaccharide. In complex type N-linked sugars, both the α3- and α6-linked mannose residues are substituted by N-acetyl-glucosamine (GlcNAc) residues. Complex type N-glycans may contain two to five GlcNAc-bearing branches that are referred to as antennae. The ultimate structure of complex type N-linked sugars may vary extensively and depends on the protein to which they are attached, on the host cell, and on the conditions under which the host cell is cultured. The GlcNAc-bearing branches may be modified with galactose (Gal) or N-acetyl-galactosamine (GalNAc) forming so-called LacNAc or LacdiNAc structures. Also, GlcNAc-bearing branches may contain multiple LacNAc structures forming so-called polylactosamine structures. Terminal galactoses may be modified with an α-2,3- or an α-2,6-linked sialic acid, whereas terminal N-acetyl-galactosomines may only be modified with an α-2,6-linked sialic acid. The addition of sialic acids to terminal Gal or GalNAc is mediated by sialyltransferases. Probably more than 20 different sialyltransferases are encoded by the human genome (Harduin-Lepers et al., 2001). They differ in substrate specificity, tissue distribution and various biochemical parameters.

Native AAT has three glycosylation sites. Thus, AAT comprises three N-linked glycans in which branching can occur. These glycans may have two, three or four so-called "antennae" or branches. Surprisingly, it has been shown that at least 10%, preferably from about 10% to about 50%, of the N-linked glycans of the rhAAT of the invention are tetra-antennary glycans. In another embodiment, at least 20% of the N-linked glycans are tetra-antennary glycans, preferably from about 20% to about 40% of the N-linked glycans are tetra-antennary glycans. It has surprisingly been shown herein that the glycosylation profile, for example, in terms of antennarity, as well as the pharmacokinetic properties, e.g., the mean residence time of the rhAAT hereof differ from plasma-derived AAT, such as PROLASTIN®.

Since full sialylation of the glycans on recombinant proteins is of importance for optimal pharmacokinetic properties, the rhAAT hereof is expressed in PER.C6® cells in combination with a sialyltransferase to achieve highly sialylated isoforms of rhAAT. PER.C6® cells thus were co-transfected with either an α-2,3 sialyltransferase (PER.C6-ST3) or an α-2,6 sialyltransferase (PER.C6-ST6). In an embodiment hereof, at least 50% of the total sialylation on the N-linked glycans is α-2,3-sialylation. For example, at least 50%, 70% or 80% of the total sialylation on the N-linked glycans is α-2,3-sialylation. In yet another embodiment, at least 90% of the total sialylation on the N-linked glycans is α-2,3-sialylation. It has surprisingly been shown that in these embodiments, the rhAAT hereof has different pharmacokinetic properties, as compared to plasma-derived AAT, such as PROLASTIN®, in particular, a prolonged mean residence time. By "sialylation" is meant the amount of sialic residues present on the AAT carbohydrate structures: "α-2,3-sialylation" means sialylation at the 2,3 position, i.e., an α-2,3-linked sialic acid (as is well known in the art) and "α-2,6-sialylation" means sialylation at the 2,6 position, i.e., or an α-2,6-linked sialic acid (also known in the art). With "at least 50% of the total sialylation on said N-linked glycans is α-2,3-sialylation," it is thus meant that at least 50% of the total number of sialic acid residues present in the rhAAT is sialylated in the 2,3 position.

It is now shown in PK studies in rat that the mean residence time (MRT) of both rhAAT produced by PER.C6-ST3 (rhAAT-ST3) and rhAAT produced by PER.C6-ST6 (rhAAT-ST6) differs significantly from that of plasma-derived AAT (PROLASTIN®). It has thus been shown that the MRT in rats of rhAAT-ST3 ranges from approximately 18-23 hours, whereas the MRT in rats of PROLASTIN® is approximately 11-12 hours. Using rhAAT having a prolonged MRT may, for example, reduce the dosage needed per patient. In contrast, the MRT in rats of rhAAT-ST6 is reduced as compared to that of PROLASTIN® (approximately 3-4 hours). The use of rhAAT-ST6 of the present invention may be advantageous due to the "more natural" 2,6-linkage of the sialic acid, which corresponds to the sialic acid linkage on plasma-derived AAT, such as PROLASTIN®. The use of rhAAT-ST6 may furthermore be advantageous in cases where a reduced MRT may be beneficial.

As stated above, the degree of sialylation of the glycans on recombinant proteins is of importance for optimal pharmacokinetic properties. The overall degree of capping with sialic acid on the N-linked glycans (as calculated by the Z/A ratio) of the rhAAT hereof may be at least 70%. The degree of capping with sialic acid on the N-linked glycans (Z/A) may be at least 80%, even more preferably, the degree of capping with sialic acid on the N-linked glycans (Z/A) is at least 90%.

In a further embodiment, the degree of capping with sialic acid on the N-linked glycans that are tetra-antennary is at least 20%, for example, between 20% and 65%. A relatively low degree of sialylation on the tetra-antennary N-glycans may yield a rhAAT product having a reduced MRT, as compared to plasma-derived AAT. In another embodiment, the degree of capping with sialic acid on the tetra-antennary N-linked glycans is at least 50%, for example, between 50% and 97%, preferably at least 60%, more preferably between 70% and 95%. The higher level of sialylation in this embodiment may contribute to the prolonged MRT, as compared to plasma-derived AAT.

Furthermore provided are preparations and pharmaceutical compositions comprising rhAAT and optionally one or more pharmaceutically acceptable excipients. By "pharmaceutically acceptable excipient" is meant any inert substance that is combined with an active molecule (such as a drug, agent, or protein) for preparing a suitable or convenient dosage form. The "pharmaceutically acceptable excipient" is an excipient that is non-toxic to recipients at the dosages and concentrations employed and is compatible with other ingredients of the formulation comprising the active molecule.

The pharmaceutical compositions can be formulated into various compositions for any route of administration well-known to the skilled person. The choice of the optimal route of administration of the pharmaceutical compositions will be influenced by several factors including, e.g., the physico-chemical properties of the active molecules within the compositions, the urgency of the clinical situation and the relationship of the plasma concentrations of the active molecules to the desired therapeutic effect. The preparations and pharmaceutical compositions of the present invention are preferably formulated for intravenous administration or aerosol administration. Pharmaceutically suitable formulations of rhAAT can be prepared according to methods known to the person skilled in the art (see *Remington's Pharmaceutical Sciences,* 18th edition, A. R. Gennaro, Ed., Mack Publishing Company (1990); *Pharmaceutical Formulation Development of Peptides and Proteins,* S. Frokjaer and L. Hovgaard, Eds., Taylor & Francis (2000); and *Handbook of Pharmaceutical Excipients,* 3rd edition, A. Kibbe, Ed., Pharmaceutical Press (2000)).

Typically, pharmaceutical compositions must be sterile and stable under the conditions of manufacture and storage. The preparations and/or pharmaceutical compositions comprising the rhAAT of the invention can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the rhAAT of the present invention can be in solution and the appropriate pharmaceutically acceptable excipient can be added and/or mixed before or at the time of delivery to provide a unit dosage-injectable form.

The rhAAT, the preparations or pharmaceutical comprising comprising rhAAT, can be used as medicaments. The rhAAT, the preparations and pharmaceutical compositions can be suitably used in the prevention and/or treatment of diseases and/or disorders for which the administration of AAT has been proven beneficial. They can inter alia be used in the prevention and/or treatment, or combination thereof, of AAT-deficiency-associated emphysema. The rhAAT, preparations or pharmaceutical compositions of the present invention can further be used in the prevention and/or treatment of smoking-related emphysema, cystic fibrosis (CF), chronic obstructive pulmonary disease (COPD). Since AAT has been described to have anti-inflammatory and antiapoptotic effects, the rhAAT, preparations or pharmaceutical compositions of the present invention may also be used as anti-inflammatory agents. (Lewis et al., 2008; Koulmanda et al., 2008.)

In a further embodiment, provided is a method for producing recombinant human α1-antitrypsin, comprising the steps of providing a PER.C6® cell with a nucleic acid encoding human α1-antitrypsin in such a way that the PER.C6® cell harbors the nucleic acid in an expressible form; and culturing the PER.C6® cell under conditions conducive to the production of recombinant human α1-antitrypsin, wherein the cell further contains a nucleic acid sequence encoding a sialyltransferase, preferably an alpha-2,6-sialyltransferase or an alpha-2,3-sialyltransferase, under control of a heterologous promoter. In an embodiment, the sialyltransferase is a human sialyltransferase. The rhAAT of the present invention may, however, also be produced in other mammalian cells, optionally co-expressing a sialyltransferase, such as, for example, 293 cells.

In an embodiment, provided is a method for producing recombinant human α1-antitrypsin, comprising the steps of providing a PER.C6® cell with a nucleic acid encoding human α1-antitrypsin in such a way that the PER.C6® cell harbors the nucleic acid in an expressible format, wherein the cell further contains a nucleic acid sequence encoding a sialyltransferase, preferably an alpha-2,6-sialyltransferase or an alpha-2,3-sialyltransferase, under control of a heterologous promoter; culturing said PER.C6® cell in a serum-free medium and allowing expression of the human α1-antitrypsin in the cell; harvesting the expressed human α1-antitrypsin from the cell and/or from the culture medium; and optionally purifying the human α1-antitrypsin.

The use of PER.C6® cells as a production platform for proteins of interest has been described in WO 00/63403, the disclosure of which is incorporated herein by reference. As shown in WO 00/63403, PER.C6® can be suitably used for the production of recombinant proteins. In order to achieve large-scale (continuous) production of recombinant proteins through cell culture, it is preferred to have cells capable of growing without the necessity of anchorage. The cells of the present invention have that capability. A PER.C6® cell according to this invention is a cell from an upstream or downstream passage or a descendent of an upstream or downstream passage of cells as deposited at the Center for Applied Microbiology and Research & European Collection of Cell Cultures (ECACC) on 29 Feb. 2006 under ECACC no. 96022940 (see, e.g., U.S. Pat. No. 5,994,128). The use of PER.C6® cells for industrial processes has been extensively described, e.g., in Nichols et al., 2002, and more in particular, for recombinant protein production, e.g., in Yallop et al., 2005a and 2005b.

The cells hereof, in particular, PER.C6® cells, have the additional advantage that they can be cultured in the absence of animal- or human-derived serum or animal- or human-derived serum components. Thus, isolation is easier, while the safety is enhanced due to the absence of additional human or animal proteins in the culture, and the system is very reliable (synthetic media are the best in reproducibility). Furthermore, the presence of the Early region 1A ("E1A") of adenovirus adds another level of advantages as compared to (human) cell lines that lack this particular gene. E1A as a transcriptional activator is known to enhance transcription from the enhancer/promoter of the CMV Immediate Early genes (Olive et al., 1990; Gorman et al., 1989). When the recombinant protein to be produced is under the control of the CMV enhancer/promoter, expression levels increase in the cells and not in cells that lack E1A.

In general, the production of a recombinant protein, such as rhAAT, in a host cell, such as a PER.C60 cell, comprises the introduction of nucleic acid in expressible format into the host cell, culturing the cells under conditions conducive to expression of the nucleic acid and allowing expression of the nucleic acid in the cells. Alternatively, a protein that is naturally expressed in desired host cells, but not at sufficient levels, may be expressed at increased levels by introducing suitable regulation sequences such as a strong promoter in operable association with the desired gene (see, e.g., WO 99/05268, where the endogenous EPO gene is over-expressed by introduction of a strong promoter upstream of the gene in human cells).

Nucleic acid encoding AAT in expressible format may be in the form of an expression cassette and usually requires sequences capable of bringing about expression of the nucleic acid, such as enhancer(s), promoter, polyadenylation signal, and the like. Several promoters can be used for expression of recombinant nucleic acid, and these may comprise viral, mammalian, synthetic promoters, and the like. In certain embodiments, a promoter driving the expression of the nucleic acid of interest is the CMV immediate early promoter, for instance, comprising nt. −735 to +95 from the CMV immediate early gene enhancer/promoter, as this promoter has been shown to give high expression levels in cells expressing E1A of an adenovirus (see, e.g., WO 03/051927). The nucleic acid of interest may be a genomic DNA, a cDNA, synthetic DNA, a combination of these, etc.

Cell culture media are available from various vendors, and serum-free culture media are nowadays often used for cell culture, because they are more defined than media-containing serum. The cells of the present invention grow well in serum-containing media as well as in serum-free media. The cells of the invention in general grow adherently in serum-containing media, but are very proficient in growing in suspension to high cell densities ($10 \times 10^6$ cells/ml and higher) in serum-free culture media, which means that they do not need a surface to adhere to, but remain relatively free from each other and from the walls of the culture vessel during most of the time. Processes for culturing the cells of the invention to high densities and/or for obtaining very high product yields from these cells have been described (WO 2004/099396).

The concept of genetic engineering to alter glycosylation of recombinant proteins produced in a cell has been amply established, and is, for instance, discussed in detail in, e.g., US 2005/0164386. To this purpose, nucleic acid encoding the desired glycosylation enzyme in expressible format is or has been introduced into the cells according to the invention, and the desired glycosylation enzyme is expressed during the culturing of the cells when the protein of interest is expressed. This results in an altered glycosylation pattern of the protein of interest as compared to the situation when no recombinant glycosylation enzyme is expressed in the cells. In the present invention, the glycosylation enzyme is a sialyltransferase, more preferably an alfa-2,3-sialyltransferase and/or an alfa-2,6-sialyltransferase. Preferably, the encoded sialyltransferase is a mammalian sialyltransferase, more preferably a human sialyltransferase. The nucleic acid encoding the sialyltransferase preferably is under control of a heterologous promoter, which should be active or have the possibility of being regulated in the cells of the invention. Preferably, the nucleic acid encoding the sialyltransferase is integrated into the genome of the cells to ensure stable inheritance, and provide for stable expression of the sialyltransferase in subsequent generations of the cells.

Furthermore, provided is recombinant human AAT, obtainable by the methods according to the invention. The rhAAT has a human glycosylation pattern different from the isolated natural human counterpart protein. Provided are rhAAT comprising N-linked glycans, wherein at least 10% of the N-linked glycans are tetra-antennary glycans. In addition, the rhAAT hereof has surprising pharmacokinetic properties.

Recombinant human AAT hereof includes full-length human AAT, but also may encompass biologically active polypeptide fragments, such as fragments of human AAT with one or more amino acid deletions at, e.g., the N-terminus of the protein, as well as biologically active variants of human AAT, such as AAT with one or more amino acid substitutions (e.g., conservative substitutions), one or more deletions or additions of amino acids, which do not significantly change the functional activity of the protein. In an embodiment, the rhAAT of the present invention comprises an amino acid sequence provided herein as SEQ ID NO:1. In some embodiments, amino acid sequences of AAT variants are at least 70%, 75%, 80%, 85%, 90%, 95%, 96%, 97%, 98% or 99% homologous to SEQ ID NO:1.

The invention is further illustrated by the following non-limiting examples.

EXAMPLES

Example 1

Cell Line Generation and Specific Productivities

Seven hundred PER.C6® cell lines expressing human AAT and co-expressing either an α-2,6-sialyltransferase (SIAT1;

NM_003032) or an α-2,3-sialyltransferase (SIAT4C; L23767) (PER.C6-AAT-ST3/PER.C6-AAT.ST6) were generated under serum-free conditions, as described in WO 2006/070011. Forty-seven serum-free PER.C6® cell lines producing either AAT-ST3 (27 cell lines) or AAT-ST6 (20 cell lines) were selected based on highest yield as determined by ELISA (AAT Elisa Kit, US Biologicals) from independent cell line generation programs using nucleofection as transfection tool. The expression plasmid contained the coding sequence for human AAT (SEQ ID NO:2) and the coding sequence for human ST3GalIV, both driven by a cytomegalovirus promoter that has been modified to achieve high levels of gene expression in PER.C6® cells (Yallop et al., 2005). The plasmid maps of the AAT expression vectors (pAATopt-ST3 and pAATopt-ST6) are shown in FIG. 9.

The productivity of the cell lines varied between 8-22 picograms per cell per day (pcd) (PER.C6-AAT-ST3) and 7-19 pcd (PER.C6-AAT-ST6) (see FIG. 1 and Tables 1 and 2). The cell lines were cryo-preserved in Proper-1 medium (Lonza) (six vials, 3-5×10⁶ cells/ml), meeting all acceptance criteria (viability>80%, good growth, two passages post-resuscitation). Batch cultures were generated (in Proper-1 medium), which were used for biochemical analysis (see Example 2).

Example 2

Biochemical Analysis

Integrity of PER.C6-rAAT

Figure 2:
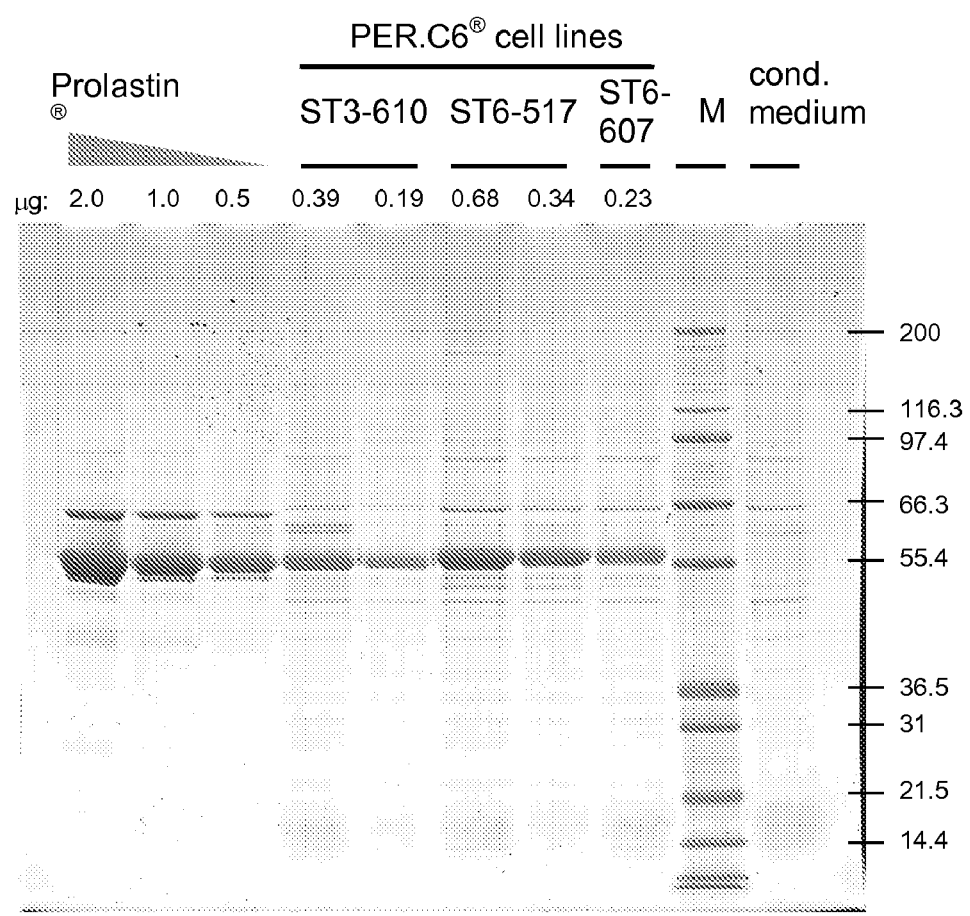
FIG. 2. 4-12% BIS-Tris SDS-PAGE gel with cell culture harvests of PER.C6-rAAT (non-purified) samples, stained with colloidal blue.

The supernatants of the 47-batch cultures were analyzed on SDS-PAGE stained with colloidal blue. Cell culture harvest of the PER.C6-rAAT (non-purified) samples showed AAT as the main protein band on SDS-PAGE. Furthermore, the gels showed intact AAT bands (shown in FIG. 2) indicating the integrity of the material.

Activity of PER.C6-rAAT

Initially (in lieu of a chromogenic activity assay), an indication for activity was determined by analyzing the formation of a complex of PER.C6-rAAT with human neutrophil elastase. To this end, cell culture harvests of PER.C6-rAAT samples were incubated with 0, 0.1, 0.2 and 0.4 µg elastase for 30 minutes at 37° C. and subsequently applied on a 4-12% BIS-Tris SDS-PAGE and stained with colloidal blue. All PER.C6-rAAT samples tested formed a complex with elastase (data not shown), indicating activity of the preparations. Further activity testing was done with a chromogenic assay based on inhibition of human neutrophil elastase using PROLASTIN® as reference (adapted from Bruin et al., 2005). All PER.C6-rAAT samples tested, except for one (PER.C6-rAAT-ST3-234c), were at least as active as PROLASTIN® (>90%) (Tables 1 and 2).

Glycan Analysis of PER.C6-rAAT

Figure 3:
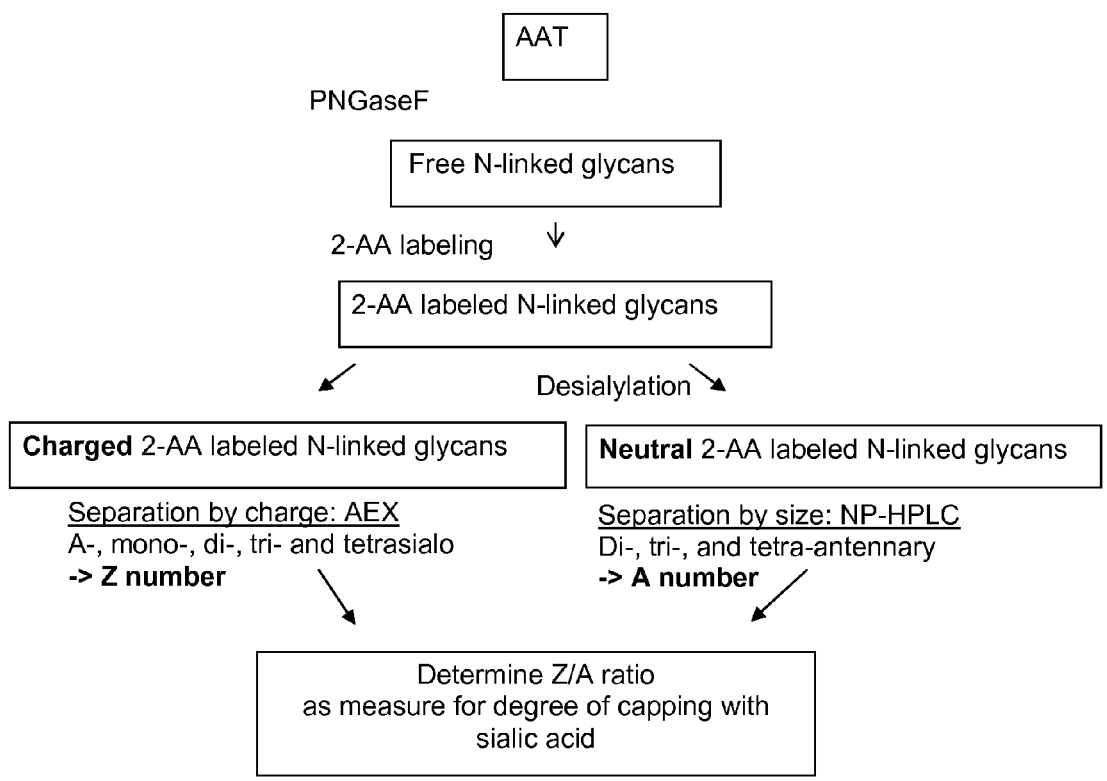
FIG. 3. Schematic overview of the assay to determine the degree of sialylation of the glycans on AAT by Z/A ratio.

To screen for PER.C6-rAAT samples of which the glycans have a relative high degree of capping with sialic acid, needed for an optimal PK profile, a lectin assay was applied, using *Erythrina cristagalli* lectin (ECL) for detection of exposed galactoses (see FIG. 3 for a schematic overview of the used assay). From the 47 samples tested, 15 showed a signal at OD405 with ECL>blank+0.2, indicating a relatively high degree of exposure of terminal galactoses on the glycans of these AAT samples. For a few of these samples, the low degree of capping of the glycans by sialic acid was confirmed by further glycan analysis using an HPLC-based method (Hermentin et al., 1996; Gervais et al., 2003). Therefore, the rhAAT samples with an ECL signal at OD405>blank+0.2 were not further subjected to extended glycan analysis and not tested in PK studies.

The extended glycan profiling method is schematically shown in FIG. 3 and involves the release of the N-linked glycans from AAT with the enzyme N-glycosidase F (PNGaseF), and labeling the glycans with fluorescent 2-anthranilic acid (2-aa). Subsequently, the glycans are separated by anion exchange chromatography (AEX) into groups according to their negative charge, i.e., separation of glycans with different numbers of sialic acid. From this profile, a Z-number, representing the degree of charge (i.e., sialylation) of the N-linked glycans, is determined.

The formula for Z:

$$Z = (A_{Asialo} \times 0) + (A_{Monosialo} \times 1)(A_{Disialo} \times 2) + (A_{Trisialo} \times 3) + (A_{Tetrasialo} \times 4)$$

(A=area, Hermentin et al., 1996).

Furthermore, the desialylated glycans are separated by normal phase chromatography (NP) into groups according to their size, i.e., separation of glycans with different degree of branching (antennarity). From this profile, an A-number, representing the degree of branching of the N-linked glycans, is determined.

The formula for A:

$$A = (A_{Diantennary} \times 2) + (A_{Triantennary} \times 3) + (A_{Tetra-antennary} \times 4)$$

Finally, by calculating the Z/A ratio, the degree (percentage) of capping by sialic acid of the N-linked glycans of a glycoprotein is obtained (Gervais et al., 2003).

Figure 4:
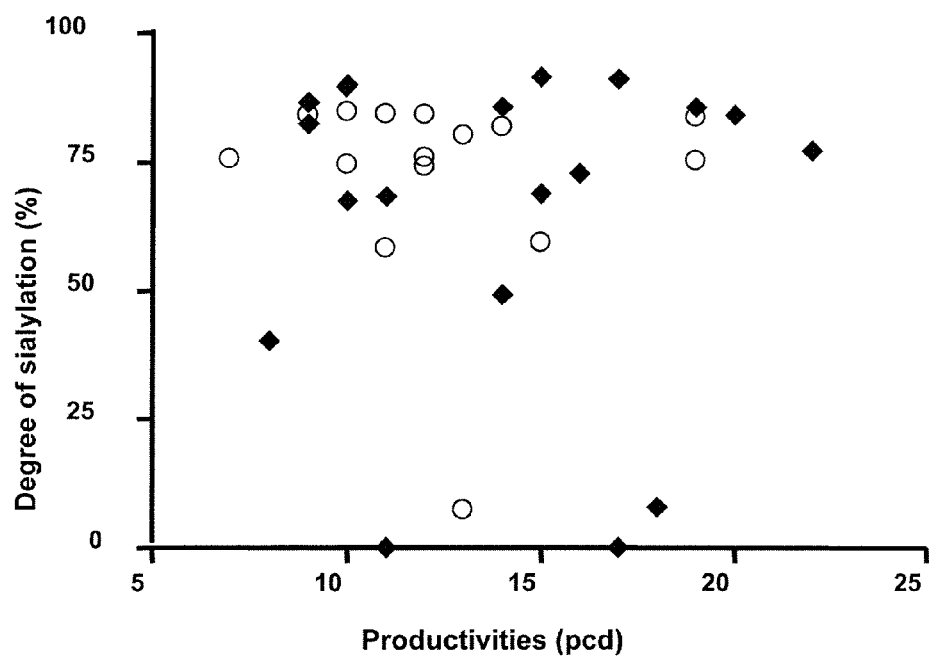
FIG. 4. Specific productivities of the PER.C6® cell lines expressing AAT are not correlated with the degree of sialylation of the glycans of PER.C6-rAAT (Spearman's r=−0.024, p=0.893). (◊: PER.C6-AAT-ST3; ○: PER.C6-AAT-ST6).

The glycan profiles of PER.C6-rAAT are shown in Tables 1 and 2. The overall profiles of PER.C6-rAAT samples (Tables 1 and 2) show 12-54% di-antennae, 13-39% tri-antennae and 22-48% tetra-antennae and 0-55% di-sialo, 0-30% tri-sialo, 0-29% tetra-sialo. The degree of capping of the glycans by sialic acid of PER.C6-rAAT ranges from 0% to 92%, this degree of capping with sialic acid is not correlated with the specific productivities of the PER.C6-rAAT cell lines (Spearman's r=−0.024, p=0.893) (Tables 1 and 2 and FIG. 4).

Figure 6:
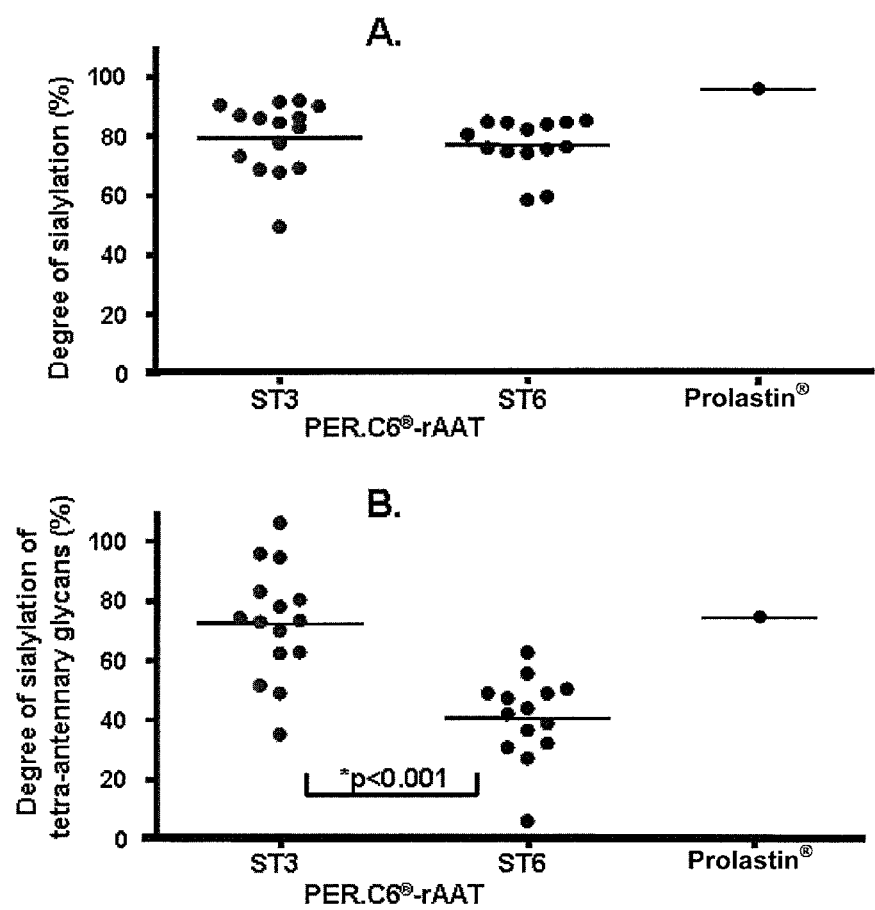
FIG. 6. Degree of sialylation on all glycans (Panel A) and on the tetra-antennary glycans (Panel B) of PER.C6-rAAT-ST3 in comparison with the glycans of PER.C6-rAAT-ST6 and PROLASTIN®.

As expected, the glycans and the ECL-positive rAAT contain a lower level of charge (sialylation) (Z-number range: 0-124) versus the ECL-negative PER.C6-rAAT (Z-number range: 151-253) (difference is significant as tested by the Mann-Whitney test, p<0.001) (see FIG. 5). The glycans of ECL-positive PER.C6-rAAT contain a higher level of antennarity (A-number range: 299-322) versus the ECL-negative PER.C6-rAAT (A-number range: 266-307) (difference is significant as tested by the Mann-Whitney test, p<0.001) (see FIG. 5). Furthermore, there is a lower degree of sialylation on the tetra-antennary glycans of PER.C6-rAAT-ST6 (ECL-negative), ranging from 6% to 62% versus PER.C6-rAAT-ST3 (ECL-negative) ranging from 35% to 106% (difference is significant as tested by the Mann-Whitney test, p<0.001), while this is not the case for the overall degree of sialylation (Tables 1 and 2, FIG. 6). The lower preference of ST6 for higher branched glycans (Joziasse et al., 1987) may be the cause of the lower degree of sialylation on the tetra-antennary glycans of PER.C6-rAAT-ST6 versus PER.C6-rAAT-ST3.

The glycan profiles indicate a tendency for a higher degree of branching on the glycans of PER.C6-rAAT in comparison to plasma-derived AAT (PROLASTIN®), as the profile for PROLASTIN® is: 80% di-antennae, 18% tri-antennae and 2% tetra-antennae (Tables 1 and 2). This phenomenon is also clear from comparison of the A-numbers (FIG. 5 and Tables 1 and 2). The degree of capping of the glycans by sialic acid of PROLASTIN® is 96% (Tables 1 and 2).

Example 3

Pharmacokinetics of PER.C6-rAAT in a Rat Model

A rat model was established to determine the pharmacokinetics (PK) of PER.C6-rAAT. The model should be able to detect AAT present in unpurified PER.C6-conditioned medium (CM) at concentrations of about 40-100 µg/mL (at 2 mL/kg resulting in doses of about 80-200 mg/kg).

Four experiments were performed: the first two to set up the model and the second, third and fourth experiments to select the PER.C6-rAAT cell lines producing rAAT with the most optimal PK characteristics. In these studies, human pdAAT (PROLASTIN®) was used to establish the model and as reference. The experimental procedure was as follows: rats (male Wistar, age 8 weeks) were dosed i.v. in the tail vein with the AAT test samples (dose volume 2 ml/kg, dose range 50-200 µg/kg, n=3 rats per group). Blood was sampled from the tail tip pre-dose and at various time points following dose administration. The blood was collected in $K_2$EDTA microvettes and plasma was prepared. The residual AAT concentration in the plasma samples was subsequently determined by ELISA (AAT Elisa Kit, Affinity Biologicals). The data obtained were modeled per rat with a two-compartment model and PK parameters were subsequently determined.

Figure 7:
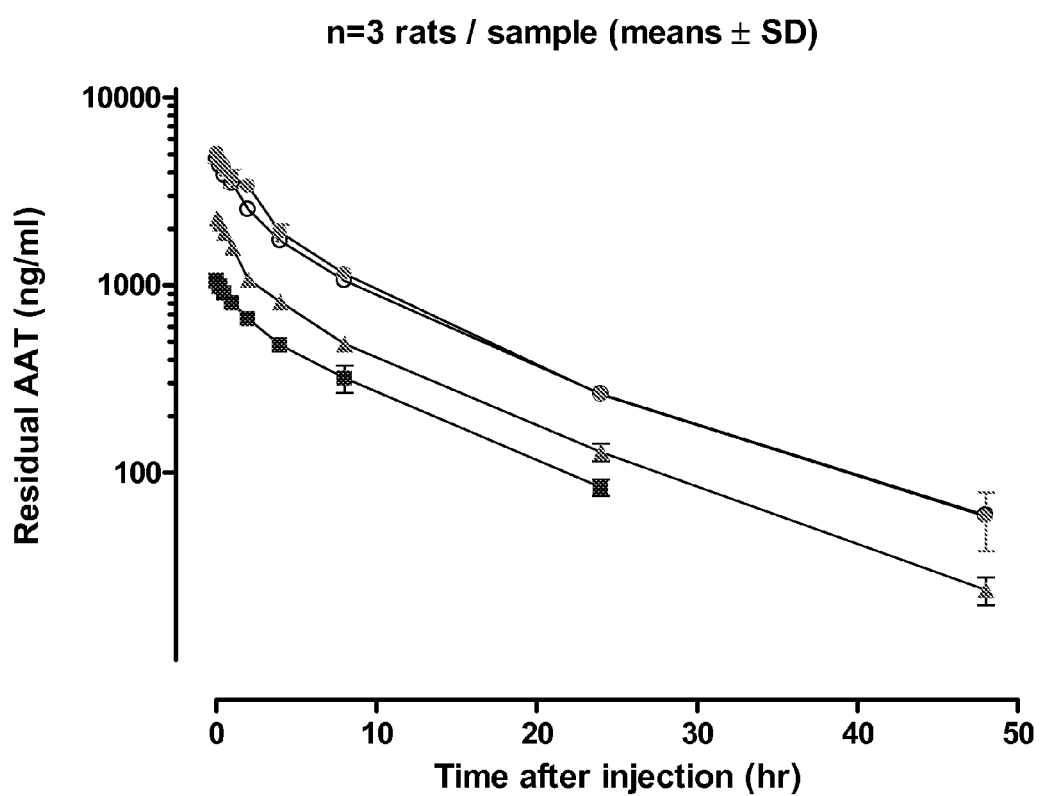
FIG. 7. Plasma concentration-time profiles for various doses of PROLASTIN® in buffer (PBS/T) or in PER.C6-CM following i.v. bolus administration to rats. ■: PROLASTIN® in PER.C6-CM, 50 µg/kg; ▲: PROLASTIN® in PER.C6-CM, 100 µg/kg; ●: PROLASTIN® in PER.C6-CM, 200 µg/kg; ○: PROLASTIN® in PBS/T, 2000 µg/kg.
Figure 8:
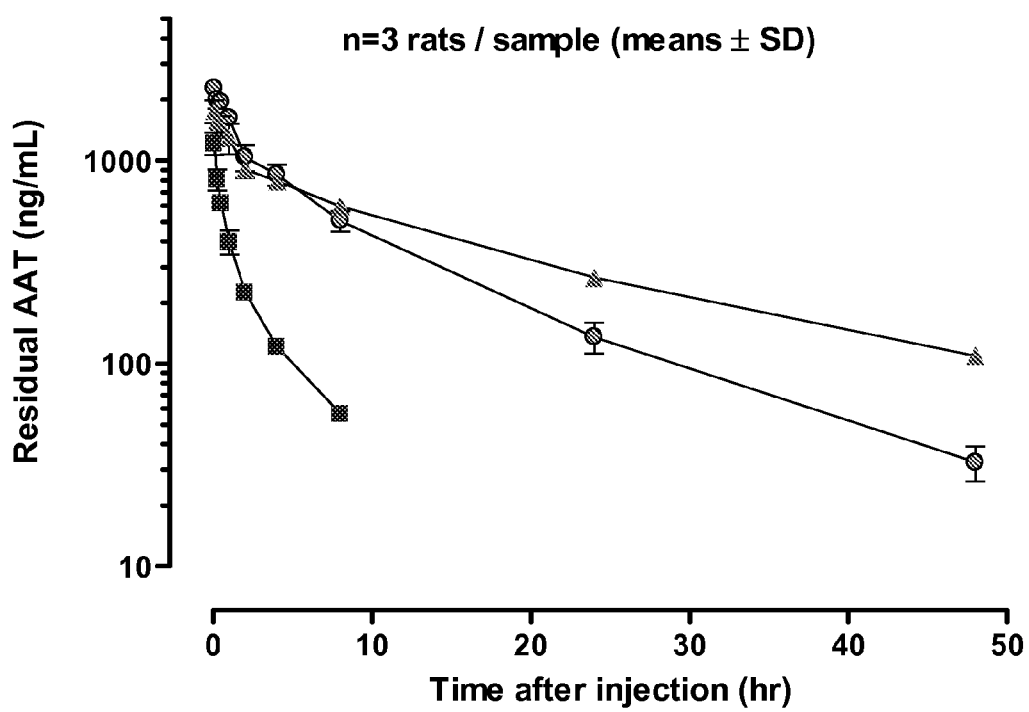
FIG. 8. Plasma concentration-time profiles for PER.C6-rAAT-ST3, PER.C6-rAAT-ST6 and PROLASTIN®. ▲: PER.C6-rAAT-ST3, MRT ~18-23 hours; ■: PER.C6-rAAT-ST6, MRT ~4-4 hours, ●: PROLASTIN®, MRT ~11-12 hours.

As shown by the data from experiment 1 (see FIG. 7), the model was found suitable to determine the PK profile in unpurified samples because the plasma concentration versus time curves of PROLASTIN® spiked in PER.C6-CM and buffer control (PBS, 0.01% w/v TWEEN®-80 (PT) (doses 200 µg/kg) are similar. A similar result was found with PROLASTIN® doses of 100 µg/kg (data not shown). In FIG. 7, it is also shown that an increased response is observed with doses of PROLASTIN® spiked in CM from 50-200 µg/kg. From the data, it was calculated that PROLASTIN® has a mean residence time (MRT) of 11-12 hours. Also, the PER.C6-rAAT samples were detected, with PER.C6-rAAT-ST3-202c showing a slower clearance (MRT~20.5 hours) as compared to PROLASTIN® and PER.C6-rAAT-ST6-530 showing a faster clearance (MRT~3.6 hours) compared to PROLASTIN® (Tables 1 and 2). Based on these observations, it was, therefore, concluded that the model could be used for the unpurified PER.C6-rAAT samples, which were tested in experiments 2-4 at a dose level of 100 µg/kg for all samples. In FIG. 8, representative PK profiles for PER.C6-rAAT-ST3 and PER.C6-rAAT-ST6 in comparison to PROLASTIN® are shown.

The last column in Tables 1 and 2 shows the MRT values obtained in the PK experiments. Statistical testing on differences between samples and groups of samples with regard to the MRT was done by ANOVA on log transformed values. The MRTs of both the PER.C6-rAAT-ST3 and PER.C6-rAAT-ST6 preparations tested were significantly different from that of PROLASTIN®. The MRT for eight out of ten PER.C6-rAAT-ST3 preparations tested were significantly higher than that of PROLASTIN® and ranged from 18-23 hours. Between these eight PER.C6-rAAT-ST3 preparations, the differences in MRT were not significant.

The MRTs of PER.C6-rAAT-ST3-053b and -539 were significantly lower than that of PROLASTIN®. For PER.C6-rAAT-ST3-0539, this is due to the relatively low degree of sialylation (49%) as confirmed by the rescue of the PK profile of this preparation in the first hour during blocking of the asialoglycoprotein receptor by co-injection with asialofetuin (data not shown). The glycan profile for PER.C6-rAAT-ST3-053b was inconclusive (no clear peak assignments possible); however, also in this case, undersialylation is most likely the cause of the low MRT.

For all PER.C6-rAAT-ST6 preparations tested, the MRT was significantly lower than that of PROLASTIN® ranging from 3.4-3.9 hours. This may be explained by the relative low degree of sialylation of the tetra-antennary glycans on PER.C6-rAAT-ST6 (ranging from 6% to 62%) and/or by a potential different mechanism of clearance for α-2,3 sialylated AAT versus α 2,6 sialylated AAT.

Conclusions

PER.C6® cell lines have been generated that produce human AAT with a high yield (up to 22 pcd) and with an acceptable quality, i.e., the preparations were active in an in vitro assay. Surprisingly and interestingly, promising PK profiles were demonstrated in a rat model. PER.C6® cells thus form a suitable platform for the production of human recombinant AAT for use in inter alia AAT-deficiency-related emphysema or for use in other inflammatory diseases with neutrophil-mediated tissue damage. The rhAAT hereof may, however, also suitably be produced in other mammalian cell types co-expressing a 2,3- or 2,6-sialyltransferases.

TABLE 1

Specific productivities, activity and glycan profiles of PER.C6 ®-rAAT-ST3

| PER.C6 ®-rAAT-ST3 cell line | QP (pcd, n = 1 or *n = 2) | Activity Ratio Cr/Ag (n = 3) | Di-antennary (%) | Tri-antennary (%) | Tetra-antennary (%) | A-number | Asialo (%) | Mono-sialo (%) |
|---|---|---|---|---|---|---|---|---|
| ECL negative cell lines ||||||||||
| 098a | 22* | 1.12 | 50.52 | 22.92 | 26.53 | 276 | 13.62 | 11.02 |
| 246c | 20* | 1.17 | 49.52 | 21.22 | 27.39 | 272 | 9.81 | 10.93 |
| 221c | 19 | 1.03 | 52.24 | 24.46 | 21.97 | 266 | 7.98 | 12.94 |
| 202c | 17* | 1.06 | 48.89 | 23.31 | 26.23 | 272 | 5.64 | 9.8 |
| 019c | 16 | 0.98 | 49.95 | 24.36 | 24.03 | 269 | 18.4 | 14.48 |
| 607 | 15 | 1.3 | 51.82 | 21.09 | 27.08 | 275 | 5.17 | 16.04 |
| 028c | 15 | 1.03 | 42.17 | 27.83 | 29.44 | 286 | 20.71 | 11.52 |
| 539 | 14 | 1.17 | 23.71 | 39.18 | 35.53 | 307 | 31.52 | 25.63 |
| 013b | 14* | 1 | 50.97 | 23.24 | 23.93 | 267 | 7.85 | 14.04 |
| 234c | 11 | 0.68 | 39.98 | 26.62 | 33.42 | 294 | 18.23 | 20.58 |
| 293c | 10* | 1.17 | 52.19 | 19.78 | 28.02 | 276 | 1.94 | 19.9 |
| 604 | 10 | 1.16 | 52.19 | 21.87 | 25.93 | 274 | 4.86 | 45.01 |
| 602 | 10 | 1.1 | 47.23 | 20 | 31.85 | 282 | 2.48 | 7.93 |
| 529 | 9* | 1.2 | 51.25 | 22.72 | 24.88 | 270 | 6.41 | 14.42 |
| 223c | 9 | 1.03 | 47.34 | 25.45 | 25.92 | 275 | 10.05 | 13.38 |
| 053b | 9 | 0.94 | ¶ | ¶ | ¶ | ¶ | ¶ | ¶ |

TABLE 1-continued

Specific productivities, activity and glycan profiles of PER.C6 ®-rAAT-ST3

ECL positive cell lines

| Cell line | | | | | | | | |
|---|---|---|---|---|---|---|---|---|
| 031c | 21 | 0.99 | | | | | | |
| 580 | 19* | 1.04 | | | | | | |
| 612 | 18* | 1.05 | 28.85 | 37.51 | 33.63 | 305 | 84.01 | 10.19 |
| 608 | 17* | 1.15 | 30.29 | 37.37 | 31.47 | 299 | >95 | |
| 045c | 14* | 1.14 | | | | | | |
| 032c | 14 | 1.08 | | | | | | |
| 534 | 11 | 0.99 | 11.66 | 35.84 | 47.7 | 322 | >95 | |
| 236c | 10 | 0.98 | | | | | | |
| 610 | 9 | 1.09 | | | | | | |
| 354b | 8 | 0.96 | 29.38 | 30.45 | 39.57 | 308 | 50.01 | 12.42 |
| 040c | | 0.98 | 23.9 | 37.18 | 36.8 | 307 | >95 | |

Plasma derived AAT (n = 2 for glycan profiles, n = 4 for PK)

| | | | | | | | | |
|---|---|---|---|---|---|---|---|---|
| Prolastin ® | na | 1 | 80.27 | 17.92 | 1.85 | 222 | 0.05 | 8.06 |

| PER.C6 ®-rAAT-ST3 cell line | Di-sialo (%) | Tri-sialo (%) | Tetra-sialo (%) | Z-number | Degree of Sia on tetra (%) | Degree of Sia Z/A (%) | MRT (hr) |
|---|---|---|---|---|---|---|---|
| *ECL negative cell lines* | | | | | | | |
| 098a | 42.23 | 14.67 | 18.46 | 213 | 69.6 | 77.2 | 18.3 |
| 246c | 39.57 | 19.82 | 19.88 | 229 | 72.6 | 84.2 | 23.2 |
| 221c | 39.4 | 22.08 | 17.6 | 228 | 80.1 | 85.7 | 18.3 |
| 202c | 40.41 | 19.43 | 24.71 | 248 | 94.2 | 91.2 | 20.5 |
| 019c | 34.36 | 17.85 | 14.9 | 196 | 62.0 | 72.9 | 21.1 |
| 607 | 28.77 | 21.39 | 28.63 | 252 | 105.7 | 91.6 | 20.2 |
| 028c | 33.3 | 19.35 | 15.11 | 197 | 51.3 | 68.9 | 21.7 |
| 539 | 15.21 | 15.23 | 12.41 | 151 | 34.9 | 49.2 | 5.1 |
| 013b | 37.47 | 22.04 | 18.59 | 229 | 77.7 | 85.8 | |
| 234c | 23.72 | 16.59 | 20.89 | 201 | 62.5 | 68.4 | |
| 293c | 31.87 | 19.54 | 26.75 | 249 | 95.5 | 90.2 | 22.5 |
| 604 | 23.21 | 14.25 | 12.63 | 185 | 48.7 | 67.5 | |
| 602 | 47.01 | 19.33 | 23.25 | 253 | 73.0 | 89.7 | |
| 529 | 38.21 | 20.39 | 20.57 | 234 | 82.7 | 86.7 | |
| 223c | 35.6 | 21.83 | 19.13 | 227 | 73.8 | 82.5 | |
| 053b | ¶ | ¶ | ¶ | ¶ | ¶ | ¶ | 5.7 |
| *ECL positive cell lines* | | | | | | | |
| 031c | | | | | | | |
| 580 | | | | | | | |
| 612 | 4.25 | 1.15 | 0.41 | 24 | 1.2 | 7.9 | |
| 608 | | | | 0 | 0.0 | 0.0 | |
| 045c | | | | | | | |
| 032c | | | | | | | |
| 534 | | | | 0 | 0.0 | 0.0 | |
| 236c | | | | | | | |
| 610 | | | | | | | |
| 354b | 14.02 | 10.63 | 12.92 | 124 | 32.7 | 40.3 | |
| 040c | | | | 0 | 0.0 | 0.0 | |

Plasma derived AAT (n = 2 for glycan profiles, n = 4 for PK)

| | | | | | | | |
|---|---|---|---|---|---|---|---|
| Prolastin ® | 71.3 | 19.23 | 1.37 | 214 | 74.3 | 96.2 | 11.2 |

¶ inconclusive glycan profile
AAT: α1-antitrypsin;
Qp: specific productivity;
pcd: picogram per cell per day;
Cr: chromogenic assay;
Ag: antigen ELISA;
Sia: sialic acid;
MRT: mean residence time;
hr: hours;
ECL: Erythrina cristagalli lectin;
PK: pharmacokinetics

TABLE 2

Specific productivities, activity and glycan profiles of PER.C6 ®-rAAT-ST6

| PER.C6 ®-rAAT-ST6 cell line | QP (pcd, n = 1 or *n = 2) | Activity Ratio Cr/Ag (n = 3) | Di-antennary (%) | Tri-antennary (%) | Tetra-antennary (%) | A-number | Asialo (%) | Mono-sialo (%) |
|---|---|---|---|---|---|---|---|---|
| ECL negative cell lines | | | | | | | | |
| 297 | 19* | 1.19 | 53.24 | 19.6 | 27.16 | 274 | 6.79 | 14.73 |
| 621 | 19 | 1.08 | 50.77 | 12.7 | 36.52 | 286 | 3.22 | 14.41 |
| 565 | 15* | 1.02 | 46.41 | 24.72 | 28.22 | 280 | 23.43 | 15.85 |
| 618 | 14 | 1.19 | 48.09 | 15.89 | 32.63 | 274 | 3.91 | 20.14 |
| 505 | 13 | 1.17 | 51.27 | 19.21 | 28.14 | 273 | 5.56 | 14.08 |
| 530 | 13* | 0.99 | | | | | | |
| 517 | 12 | 1.12 | 54.26 | 18.44 | 27.3 | 273 | 4.38 | 11.35 |
| 506 | 12 | 1.06 | 48.37 | 17.77 | 33.11 | 282 | 3.58 | 12.71 |
| 560 | 12* | 0.94 | 47.2 | 23.6 | 28.04 | 277 | 7.2 | 13.32 |
| 607 | 11 | 0.95 | 46.24 | 20.78 | 32.98 | 287 | 15.61 | 38.38 |
| 035c | 11 | 1.11 | 49.29 | 16.72 | 33.19 | 282 | 2.05 | 9.75 |
| 514 | 10 | 0.99 | 52.74 | 18.66 | 28.6 | 276 | 3.85 | 16.86 |
| 537 | 10 | 0.93 | 48.23 | 20.07 | 30.22 | 278 | 8.35 | 16.34 |
| 084c | 9 | 1.05 | 49.45 | 17.59 | 32.47 | 283 | 1.79 | 10.21 |
| 613 | 8 | 1.13 | ¶ | ¶ | ¶ | ¶ | ¶ | ¶ |
| 617 | 7 | 0.98 | 52.52 | 19.79 | 27.68 | 275 | 5.55 | 22.6 |
| ECL positive cell lines | | | | | | | | |
| 529 | 13 | 1.09 | 24.91 | 37.46 | 37.59 | 313 | 83.59 | 11.62 |
| 548 | 11* | 1.01 | | | | | | |
| 66 | 11 | 0.96 | 23.23 | 33.13 | 43.64 | 320 | 55.01 | 23.54 |
| 528 | 10 | 0.98 | | | | | | |
| Plasma derived AAT (n = 2 for glycan profiles, n = 4 for PK) | | | | | | | | |
| Prolastin ® | na | 1 | 80.27 | 17.92 | 1.85 | 222 | 0.05 | 8.06 |

| PER.C6 ®-rAAT-ST6 cell line | Di-sialo (%) | Tri-sialo (%) | Tetra-sialo (%) | Z-number | Degree of Sia on tetra (%) | Degree of Sia Z/A (%) | MRT (hr) |
|---|---|---|---|---|---|---|---|
| ECL negative cell lines | | | | | | | |
| 297 | 52.85 | 17.41 | 8.22 | 206 | 30.3 | 75.2 | |
| 621 | 40.6 | 23.5 | 18.27 | 239 | 50.0 | 83.6 | 3.4 |
| 565 | 39.59 | 13.6 | 7.53 | 166 | 26.7 | 59.3 | |
| 618 | 39.45 | 20.69 | 15.81 | 224 | 48.5 | 81.8 | 3.8 |
| 505 | 47.77 | 20.76 | 11.72 | 219 | 41.6 | 80.2 | |
| 530 | | | | | | | 3.6 |
| 517 | 49.29 | 19.93 | 15.07 | 230 | 55.2 | 84.2 | |
| 506 | 51.53 | 30.32 | 1.86 | 214 | 5.6 | 75.9 | |
| 560 | 55.33 | 15.24 | 8.92 | 205 | 31.8 | 74.0 | |
| 607 | 21.7 | 11.64 | 12.66 | 167 | 38.4 | 58.2 | |
| 035c | 52.61 | 19.46 | 16.13 | 238 | 48.6 | 84.4 | |
| 514 | 38.6 | 22.87 | 17.81 | 234 | 62.3 | 84.8 | 3.9 |
| 537 | 45.96 | 18.39 | 10.95 | 207 | 36.2 | 74.5 | |
| 084c | 51.4 | 21.37 | 15.23 | 238 | 46.9 | 84.1 | |
| 613 | ¶ | ¶ | ¶ | ¶ | ¶ | ¶ | |
| 617 | 41.75 | 18.06 | 12.03 | 208 | 43.5 | 75.6 | |
| ECL positive cell lines | | | | | | | |
| 529 | 3.64 | 0.68 | 0.46 | 23 | 1.2 | 7.3 | |
| 548 | | | | | | | |
| 66 | 13.09 | 4.87 | 3.49 | 78 | 8.0 | 24.4 | |
| 528 | | | | | | | |
| Plasma derived AAT (n = 2 for glycan profiles, n = 4 for PK) | | | | | | | |
| Prolastin ® | 71.3 | 19.23 | 1.37 | 214 | 74.3 | 96.2 | 11.2 |

¶ inconclusive glycan profile
AAT: α1-antitrypsin;
Qp: specific productivity;
pcd: picogram per cell per day;
Cr: chromogenic assay;
Ag: antigen ELISA;
Sia: sialic acid;
MRT: mean residence time;
hr: hour;
ECL: Erythrina cristagalli lectin;
PK: pharmacokinetics

REFERENCES

A. Gervais, V. A. Hammel, S. Pelloux, P. Lepage, G. Baer, N. Carte, O, Sorokine, J. M. Strub, R. Koerner, E. Leize and A. Van Dorsselaer, 2003. Glycosylation of human recombinant gonadotrophins: characterization and batch-to-batch consistency. *Glycobiology* 13:179-189.

P. Hermentin, R. Witzel, E. J. Kanzy, G. Diderich, D. Hoffmann, H. Metzner, J. Vorlop and H. Haupt, 1996. The hypothetical N-glycan charge: a number that characterizes protein glycosylation. *Glycobiology* 6:217-230.

D. H. Joziasse, W. E. Schiphorst, D. H. Van den Eijnden, J. A. Van Kuik, H. Van Halbeek and J. F. Vliegenthart, 1987. Branch specificity of bovine colostrum CMP-sialic acid: Gal beta 1-4GlcNAc-R alpha 2-6-sialyltransferase. Sialylation of bi-, tri-, and tetraantennary oligosaccharides and glycopeptides of the N-acetyllactosamine type. *J. Biol. Chem.* 262: 2025-2033.

E. Karnaukhova, Y. Ophir and B. Golding, 2006. Recombinant human alpha-1 proteinase inhibitor: towards therapeutic use. *Amino Acids* 30:317-332.

A. T. Mulgrew, C. C. Taggart and N. G. McElvaney, 2007. Alpha-1-Antitrypsin Deficiency-Current Concepts. *Lungs* 185:191-201.

T. L. Spencer, J. E. Humphries and M. L. Brantly, 2005. Antibody Response to Aerosolized Transgenic Human Alpha1 Antitrypsin. *N.E.J.M.* 352:30-31.

C. A. Yallop, J. Crowley, J. Cote, K. Hegmans-Brouwer, F. Lagerwerf, R. Gagne, J. C. Martin, N. Oosterhuis, D. J. Opstelten and A. Bout, 2005a. PER.C6® cells for the manufacture of biopharmaceutical proteins. In *Modern Biopharmaceuticals*, Volume 3, Design, Development and Optimization," pp. 779-807. Wiley-VCH, Germany.

C. Yallop, M. Raadsman, M. Zuiderwijk, Y. Van Noordenburg, A. Vooys, R. Keehnen, B. Van Montfort, M. Jansen, F. Lagerwerf, R. Dijkstra and others, 2005b. High-level production of recombinant IgG in the human cell line PER.C6®. In: F. Godia and M. Fussenegger, editors. Animal cell technology meets genomics: Springer, pp. 533-536.

E. C. Bruin, D. Roem, I. Bulder, M. Dieker, G. Voerman, C. E. Hack, 2005. Production, purification and characterization of recombinant Fahsin, a novel antistasin-type proteinase inhibitor. *FEMS Yeast Res.* 5(11):1069-1077.

A. Varki, R Cummings, J. Esko, H. Freeze, G. Hart, J. Marth, 1999. Essentials of glycobiology. Cold Spring Harbor Laboratory Press, Cold Spring Harbor, N.Y., USA.

A. Harduin-Lepers, V. Vallejo-Ruiz, Krzewinsky-Recchi Mass., B. Samyn-Petit, S. Julien, P. Delannoy, 2001. The human sialyltransferase family. *Biochimie* 83:727-737.

E. C. Lewis, M. Mizrahi, M. Toledano, N. DeFelice, J. L. Wright, A. Churg, L. Shapiro, C. A. Dinarello, 2008. α1-Antitrypsin monotherapy induces immune tolerance during islet allograft transplantation in mice. *PNAS* 105: 16236-16241.

M. Koulmanda, M. Bhasin, L. Hoffman, Z. Fan, A. Qipo, H. Shi, S. Bonner-Weir, P. Putheti, N. Degauque, T. A. Libermann, H. Auchincloss, Jr., J. S. Flier, T. B. Strom, 2008. Curative and β cell regenerative effects of α1-antitrypsin treatment in autoimmune diabetic NOD mice. *PNAS* 105: 16242-16247.

W. W. Nichols, R. Lardenoie, B. J. Ledwith, K. Brouwer, S. Manam, R. Vogels, D. Kaslow, D. Zuidgeest, A. J. Bett, J. Chen and others, 2002. Propagation of adenoviral vectors: use of PER.C6® cells. In: D. Curiel and J. T. Douglas, editors. Adenoviral vectors for gene therapy. San Diego: Elsevier. pp. 129-167.

D. M. Olive, W. Al-Mulla, M. Simsek, S. Zarban, W. al-Nakib, 1990. The human cytomegalovirus immediate early enhancer-promotor is responsive to activation by the adenovirus-5 13S E1A gene. *Arch. Virol.* 112:67-80.

C. M. Gorman, D. Gies, G. McGray, M. Huang. 1989. The human cytomegalovirus major immediate early promoter can be transactivated by adenovirus early proteins. *Virology* 171:377-385.

---

The invention claimed is:

1. Recombinant human α1-antitrypsin (rhAAT) comprising N-linked glycans, characterized in that:
   (a) at least 10% of said N-linked glycans are tetra-antennary glycans; and
   (b) the degree of capping with sialic acid on said N-linked glycans (Z/A) is at least 50%.

2. The rhAAT according to claim 1, wherein at least 20% of said N-linked glycans are tetra-antennary glycans.

3. The rhAAT according to claim 1, wherein from about 10% to 50% of said N-linked glycans are tetra-antennary glycans.

4. The rhAAT according to claim 1, wherein from about 20% to 40% of said N-linked glycans are tetra-antennary glycans.

5. The rhAAT of claim 1, wherein at least 50% of the total sialylation on said N-linked glycans is α-2,3-sialylation.

6. The rhAAT according to claim 5, wherein at least 90% of the total sialylation on said N-linked glycans is α-2,3-sialylation.

7. The rhAAT of claim 1, wherein the degree of capping with sialic acid on said N-linked glycans (as calculated by the Z/A ratio) is at least 70%.

8. The rhAAT of claim 1, wherein the degree of capping with sialic acid on said N-linked glycans that are tetra-antennary is at least 20%.

9. The rhAAT of claim 1, wherein the degree of capping with sialic acid on said N-linked glycans that are tetra-antennary is at least 50%.

10. The rhAAT according to claim 9, wherein the degree of capping with sialic acid on said N-linked glycans that are tetra-antennary is from about 50% to about 97%.

11. The rhAAT of claim 1, wherein the degree of capping with sialic acid on said N-linked glycans that are tetra-antennary is from about 70% to about 95%.

12. The rhAAT of claim 1, further comprising a pharmaceutically acceptable excipient.

13. A method of preventing or treating chronic obstructive pulmonary disease, the method comprising:
   Utilizing the rhAAT of claim 1 in the prevention and/or treatment of emphysema.

14. The rhAAT of claim 7, wherein the degree of capping with sialic acid on the N-linked glycans (as calculated by Z/A ratio) is at least 80%.

15. The rhAAT of claim 14, wherein the degree of capping with sialic acid on the N-linked glycans (as calculated by Z/A ratio) is at least 90%.

16. Recombinant human α1-antitrypsin comprising N-linked glycans, wherein:
   at least 20% of the N-linked glycans are tetra-antennary glycans; and
   having a degree of capping with sialic acid on the N-linked glycans, as calculated by the Z/A ratio, of at least 90%.

17. The recombinant human α1-antitrypsin of claim 16, wherein at least 50% of the total sialylation on the N-linked glycans is α-2,3-sialylation.

* * * * *

SEQUENCE LISTING

```
<160> NUMBER OF SEQ ID NOS: 2

<210> SEQ ID NO 1
<211> LENGTH: 418
<212> TYPE: PRT
<213> ORGANISM: Homo sapiens

<400> SEQUENCE: 1

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110
```

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
        130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
        275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys

<210> SEQ ID NO 2
<211> LENGTH: 1257
<212> TYPE: DNA
<213> ORGANISM: Homo sapiens

<400> SEQUENCE: 2

```
atgcccagca gcgtgagctg gggcatcctg ctgctggccg gcctgtgctg cctggtgccc     60
gtgagcctgg ccgaggaccc ccagggcgac gccgcccaga aaaccgacac cagccaccac    120
gaccaggacc accccacctt caacaagatc ccccccaacc tggccgagtt cgccttcagc    180
ctgtaccggc agctggccca ccagagcaac agcaccaaca tcttttttca gcccgtgagc    240
atcgccaccg ccttcgccat gctgtccctg ggcaccaagg ccgacaccca cgacgagatc    300
ctggaaggcc tgaacttcaa cctgaccgag atccccgagg cccagatcca cgagggcttc    360
```

```
caggaactgc tgcggaccct gaaccagccc gacagccagc tccagctcac caccggcaac    420
ggcctgtttc tgagcgaggg cctgaaactg gtggacaagt ttctcgaaga tgtgaagaag    480
ctgtaccaca gcgaggcctt caccgtgaac ttcggcgaca ccgaggaagc caagaagcag    540
atcaacgact acgtggagaa gggcacccag ggcaagatcg tggacctggt gaaagagctg    600
gaccgggaca ccgtgttcgc cctggtgaac tacatcttct tcaagggcaa gtgggagcgg    660
cctttcgagg tgaaggatac cgaggaagag gacttccacg tggaccaggt gaccaccgtg    720
aaggtgccca tgatgaagcg gctgggcatg ttcaacatcc agcactgcaa gaagctgtcc    780
agctgggtcc tgctgatgaa gtacctgggc aacgccaccg ccatcttttt tctgcccgac    840
gagggcaagc tgcagcacct ggaaaacgag ctgacccacg acatcatcac caagtttctg    900
gaaaatgagg accggcggag cgccagcctg cacctgccca agctgtccat caccggcacc    960
tacgacctga agagcgtgct gggccagctg ggcatcacca aggtgttcag caacggcgcc   1020
gacctgagcg gcgtgaccga agaggccccc ctgaagctgt ctaaggccgt gcacaaggcc   1080
gtgctgacca tcgacgagaa ggggaccgaa gccgccggag ccatgtttct ggaagccatc   1140
cccatgagca tcccccccga ggtgaagttc aacaagccct tcgtgttcct gatgatcgag   1200
cagaacacca agagccccct gttcatgggc aaggtggtga accccaccca aaagtga      1257
```